(12) United States Patent
Liu et al.

(10) Patent No.: US 10,093,936 B2
(45) Date of Patent: Oct. 9, 2018

(54) **RECOMBINANT *BACILLUS SUBTILIS* FOR PRODUCING ACETYLGLUCOSAMINE AND CONSTRUCTION METHOD THEREOF**

(71) Applicant: Jiangnan University, Wuxi, Jiangsu (CN)

(72) Inventors: Long Liu, Jiangsu (CN); Jian Chen, Jiangsu (CN); Guocheng Du, Jiangsu (CN); Jianghua Li, Jiangsu (CN); Tengfei Niu, Jiangsu (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 15/390,490

(22) Filed: Dec. 24, 2016

(65) Prior Publication Data

US 2018/0171343 A1 Jun. 21, 2018

(30) Foreign Application Priority Data

Dec. 20, 2016 (CN) .......................... 2016 1 1183770

(51) Int. Cl.
*A61K 39/40* (2006.01)
*C12N 15/75* (2006.01)
*C12N 15/10* (2006.01)
*C12N 15/113* (2010.01)

(52) U.S. Cl.
CPC ........... *C12N 15/75* (2013.01); *C12N 15/102* (2013.01); *C12N 15/113* (2013.01); *C12N 2310/12* (2013.01)

(58) Field of Classification Search
None
See application file for complete search history.

(56) References Cited

U.S. PATENT DOCUMENTS

2012/0009627 A1* 1/2012 Deng .................... C12N 15/52
435/84
2015/0072898 A1* 3/2015 Moerschbacher ..... C12N 15/65
506/26

OTHER PUBLICATIONS

Liu et al. Metabolic Engineering vol. 23, 2014.*

* cited by examiner

*Primary Examiner* — Jana A Hines
*Assistant Examiner* — Khatol S Shahnan Shah
(74) *Attorney, Agent, or Firm* — SZDC Law P.C.

(57) ABSTRACT

The present invention provides a recombinant *Bacillus subtilis* for producing acetylglucosamine and construction method thereof. The recombinant *Bacillus subtilis* is obtained by deletion of glmS ribozyme of *Bacillus subtilis* for regulating expression of glucosamine synthase, and insertion of a terminator and a constitutive promoter. The method comprises constructing a deleting cassette of a glmS ribozyme encoding gene, which includes an upstream homologous fragment, a resistance gene, a terminator sequence, a constitutive promoter sequence and a downstream homologous fragment in sequence; and transforming the deleting cassette into *Bacillus subtilis*, to obtain the recombinant *Bacillus subtilis*. In the invention, glucosamine synthase gene (glmS) ribozyme is deleted by homologous recombination, and in host cells, GlcN6P feedback inhibition of expression of glucosamine synthase gene glmS is blocked, and the accumulation of acetylglucosamine is improved.

7 Claims, 1 Drawing Sheet
Specification includes a Sequence Listing.

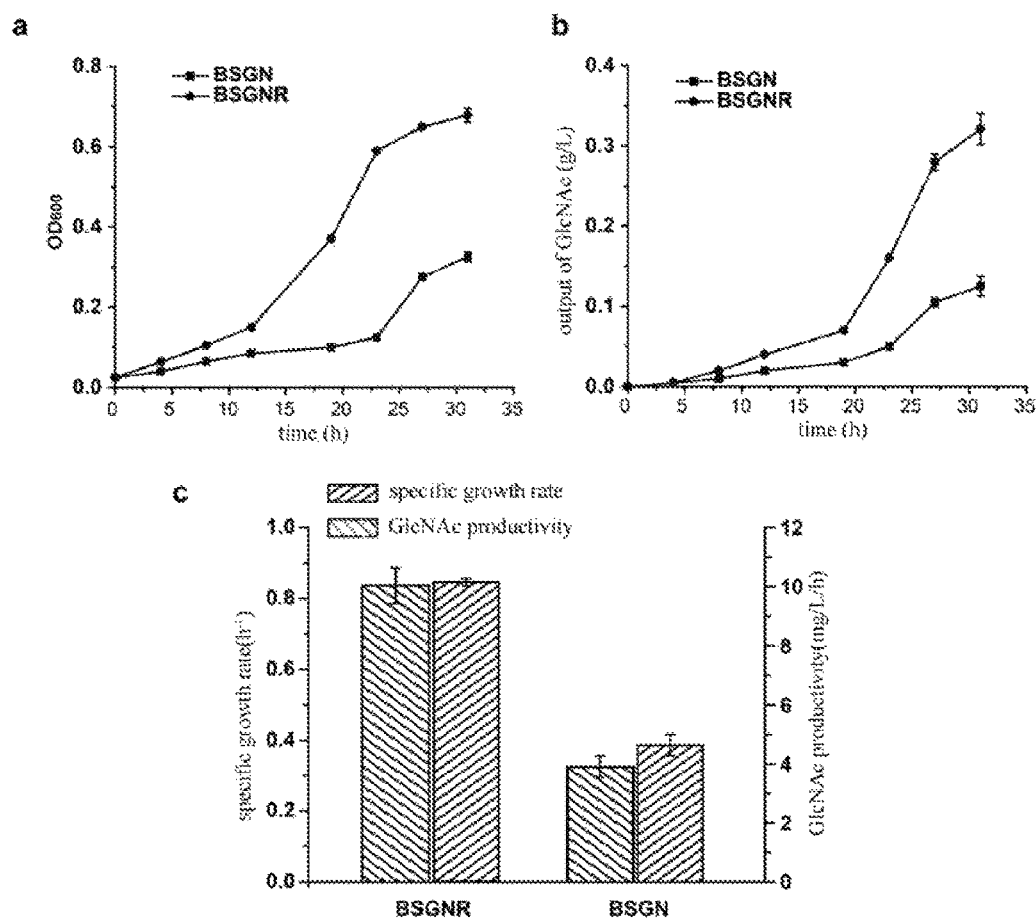

US 10,093,936 B2

RECOMBINANT *BACILLUS SUBTILIS* FOR PRODUCING ACETYLGLUCOSAMINE AND CONSTRUCTION METHOD THEREOF

FIELD OF THE INVENTION

The present invention relates to the field of genetic engineering, and more particularly to a recombinant *Bacillus subtilis* for producing acetylglucosamine and construction method thereof.

DESCRIPTION OF THE RELATED ART

GlcNAc is a pharmaceutically and nutraceutically useful compound, which was widely used for treatment of osteoarthritis and maintaining health of the joint. Previously a *Bacillus subtilis* strain has been constructed for efficient production of GlcNAc. However, slow cell growth and low GlcNAc titer in industrial relevant minimal medium of engineered *B. subtilis* restricts the application for industrial production. To move a step forward for microbial GlcNAc fermentation in industrial conditions, cell growth and GlcNAc titer should be enhanced. And, the further improvement of GlcNAc titer is limited by the glmS ribozyme feedback inhibition. The ribozyme can cleave the messenger RNA of the glmS gene in Gram-positive bacteria. It is activated by glucosamine-6-phosphate (GlcN6P) which is the metabolic product of the GlmS enzyme to stimulate autocatalytic site-specific cleavage. The metabolite-induced self-cleavage specifically targets the downstream transcript for intracellular degradation. This degradation pathway relies on action of Rnase J1. Rnase J1 specifically degrades products with a 5' hydroxyl terminal arisen from site-specific cleavage. And the ribozyme serves as a metabolite-responsive genetic switch that represses the glmS gene in response to rising glucosamine-6-phosphate (GlcN6P) concentrations. To overproduce GlcNAc, glmS ribozyme feedback inhibition should be released.

SUMMARY OF THE INVENTION

An object of the present invention is to provide a recombinant *Bacillus subtilis* for producing acetylglucosamine and construction method thereof. In the invention, glucosamine synthase glmS ribozyme is deleted by homologous recombination to block glmS ribozyme feedback inhibition, and promote the accumulation of acetylglucosamine.

For the above purpose, the invention provides the following technical solutions.

In one aspect, the invention provides a recombinant *Bacillus subtilis* for producing acetylglucosamine, wherein the recombinant *Bacillus subtilis* is obtained by deletion of glmS ribozyme of *Bacillus subtilis* for adjusting expression of glucosamine synthase, and insertion of a terminator and a constitutive promoter.

In an embodiment, the *Bacillus subtilis* is BSGN6-$P_{xylA}$-glmS-$P_{43}$-GNA1 (referred to as "BSGN" herein), which is obtained by expression of glmS, GNA1 under control of promoters $P_{xylA}$, $P_{43}$ respectively. *B. subtilis* 168ΔnagPΔgamPΔgamAΔnagAΔnag-BΔldhΔpta::lox72 is used as a host.

In an embodiment, the encoding gene of the glmS ribozyme is shown in NCBI-Gene ID: 8302932.

Preferably, the terminator is a trp terminator, a ybc terminator or a T7 terminator.

Preferably, the constitutive promoter is a P43 promoter, a PsrfA promoter or a PaprE promoter.

In another aspect, the invention provides a construction method of a recombinant *Bacillus subtilis* for producing acetylglucosamine, the method comprises the following steps:

(1) constructing a deleting cassette of a glmS ribozyme encoding gene, wherein the deleting cassette includes an upstream homologous fragment, a resistance gene, a terminator sequence, a constitutive promoter sequence and a downstream homologous fragment in sequence; and (2) transforming the deleting cassette of the step (1) into *Bacillus subtilis*, to obtain the recombinant *Bacillus subtilis* through screening and PCR validation.

Preferably, the resistance gene is a spectinomycin resistance gene spc, a bleomycin resistance gene zeo, a kanamycin resistance gene kan, or an ampicillin resistance gene amp.

Preferably, the terminator is a trp terminator, a ybc terminator or a T7 terminator.

Preferably, the encoding gene of the glmS ribozyme is shown in NCBI-Gene ID: 8302932.

Preferably, the constitutive promoter is a P43 promoter, a PsrfA promoter or a PaprE promoter.

In a specific embodiment, the *Bacillus subtilis* is BSGN6-$P_{xylA}$-glmS-$P_{43}$-GNA1 (referred to as "BSGN" herein), which is obtained by expression of glmS, GNA1 under control of promoters $P_{xylA}$, $P_{43}$ respectively, wherein *B. subtilis* 168ΔnagPΔgamPΔgamAΔnagAΔnagBΔldhΔpta::lox72 is used as a host.

The construction method of BSGN is referred to the reference "Modular pathway engineering of *Bacillus subtilis* for improved N-acetylglucosamine production (Metabolic Engineering, 23(2014) p 42-52)", and will not be described in more detail herein.

In still other aspect, the invention provides use of the recombinant *Bacillus subtilis* in fermentation production of acetylglucosamine.

Preferably, the fermentation medium comprises glucose, $Na_2HPO_4$, $KH_2PO_4$, $(NH_4)_2SO_4$, $MgSO_4$, $FeSO_4 \cdot 7H_2O$, $MnSO_4 \cdot 4H_2O$, thymine and tryptophan.

In a specific embodiment, by weight, the fermentation medium comprises glucose 2.0 g/L, $Na_2HPO_4$ 7.1 g/L, $KH_2PO_4$ 1.35 g/L, $(NH_4)_2SO_4$ 2 g/L, $MgSO_4$ 0.25 g/L, $FeSO_4 \cdot 7H_2O$ 1.0 g/L, $MnSO_4 \cdot 4H_2O$ 0.1 g/L, thymine 0.01 g/L and tryptophan 0.01 g/L.

By means of the above technical solutions, as compared with the prior art the invention has the following advantages:

In the invention, *Bacillus subtilis* (BSGN6-$P_{xylA}$-glmS-$P_{43}$-GNA1) is used as an original strain, glucosamine synthase glmS ribozyme is deleted by homologous recombination, and in host cells, GlcN6P feedback inhibition of expression of glucosamine synthase gene glmS is blocked, thereby promoting the accumulation of acetylglucosamine. The recombinant *Bacillus subtilis* of the invention can improve the output of acetylglucosamine while the minimal medium is used. In a specific embodiment, the specific growth rate and the output of acetylglucosamine reach 0.84 $h^{-1}$ and 321.3 mg/L respectively, which are 2.09-fold and 2.57-fold of the original strain respectively, this will lay a foundation for producing glucosamine from genetically engineered *Bacillus subtilis*. The recombinant *Bacillus subtilis* of the invention is constructed conveniently, easy to use, and has a good application prospect.

BRIEF DESCRIPTION OF THE DRAWINGS

FIG. 1 shows the effects of deletion of glmS ribozyme on cell growth and production of N-acetylglucosamine (GlcNAc).

DESCRIPTION OF THE PREFERRED EMBODIMENTS

The invention will be further illustrated in more detail with reference to the accompanying drawing. It is noted that, the following embodiments only are intended for purposes of illustration and are not intended to limit the scope of the invention.

Embodiment 1

The amplification primers of the deleting cassette are designed based on the up-stream and down-stream sequences of glms ribozyme encoding gene of *Bacillus subtilis* (*Bacillus subtilis* 168, available from American Type Culture Collection, ATCC No. 27370) published in NCBI.

The up-stream homologous fragment primers were:

```
GlmS-F
                                          (SEQ ID No. 1)
TCTGCTATTATGCTGATGAACAC;

GlmS-1R
                                          (SEQ ID No. 2)
GGAATACTCAAAAAAGCCCGCTCATTAGGCGGGCTGCCTTTTTCCGGG
CGCTTAGTT.
```

The screening marker expression cassette primers were:

```
GlmS-2F
                                          (SEQ ID No. 3)
GGAAAAAGGCAGCCCGCCTAATGAGCGGGCTTTTTTGAGTATTCCAAA

CTGGACACATGG;

GlmS-2R
                                          (SEQ ID No. 4)
ATCAAACTAAGCGCCCGGAAAAAGGCAGCCCGCCAGTGTTTCCACCA

TTTTTTCAATTT.
```

The P43 promoter primers were:

```
GlmS-3F
                                          (SEQ ID No. 5)
GAAACACTGGCGGGCTGCCTTTTTCCGGGCGCTTAGTTTGATAGGTG

GTATGTTTTCGC;

GlmS-3R
                                          (SEQ ID No. 6)
CGTCCCCTCCTACATGTTTTTATAATGGTACCGCTATCAC.
```

The down-stream homologous fragment primers were:

```
GlmS-4F
                                          (SEQ ID No. 7)
GTGATAGCGGTACCATTATAAAAACATGTAGGAGGGGACG;

GlmS-R
                                          (SEQ ID No. 8)
TTCTGTCTCAAGTCCTCCATTGACG.
```

An up-stream homologous fragment, a P43 promoter and a down-stream homologous fragment were amplified from the genome of *Bacillus subtilis* by using the above primers, and a screening marker expression cassette containing spectinomycin resistance gene was amplified from the vector PDGREF. The trp terminator sequence (AGCCCGC-CTAATGAGCGGGCTTTTTT, SEQ ID No. 27) was inserted into the primer GlmS-2F (SEQ ID No. 3). The up-stream homologous fragment, the screening marker, the P43 promoter and the down-stream homologous fragment were fused by fusion PCR technology, and a deleting cassette of glmS ribozyme encoding gene was obtained. The deleting cassette was amplified using the primer GlmS-F/GlmS-R, the obtained deleting cassette was transformed into *Bacillus subtilis* BSGN, BSGN was obtained by controlling recombinant expression of glmS, GNA1 by promoters of $P_{xylA}$, $P_{43}$ respectively, taking *B. subtilis* 168ΔnagPΔgamPΔgamAΔnagAΔnagBΔldhΔpta::lox72 as a host. The correct transformants were screened and determined by PCR validation. mazF was induced to express, and the strains without resistance were screened, it was determined that the glmS ribozyme encoding gene was deleted successfully and the recombinant *Bacillus subtilis* BSGNR was obtained.

In this embodiment 1, the amplification conditions are as follows: pre-denaturation at 98° C. for 3 minutes; 34 cycles of (denaturation at 98° C. for 10 seconds, annealing at 55° C. for 5 seconds, and elongation at 68° C. for 1.2 min), and elongation at 68° C. for 5 minutes.

Embodiment 2

The amplification primers of the deleting cassette were designed based on the up-stream and down-stream sequences of glms ribozyme encoding gene of *Bacillus subtilis* (*Bacillus subtilis* 168, available from American Type Culture Collection, ATCC No. 27370) published in NCBI.

The up-stream homologous fragment primers were:

```
GlmS-F
                                          (SEQ ID No. 1)
TCTGCTATTATGCTGATGAACAC;

GlmS-1R
                                          (SEQ ID No. 9)
GGAATACTCAAAAAACCCCTCAAGACCCGTTTAGAGGCCCCAAGGGGT

TATGCTAGCCTTTTTCCGGGCGCTTAGTT.
```

The screening marker expression cassette primers were:

```
GlmS-2F
                                          (SEQ ID No. 10)
GGAAAAAGGCTAGCATAACCCCTTGGGGCCTCTAAACGGGTCTTGA

GGGGTTTTTTGAGTATTCCAAACTGGACACATGG;

GlmS-2R
                                          (SEQ ID No. 11)
ATCAAACTAAGCGCCCGGAAAAAGGCAGCCCGCCAGTGTTTCCACCA

TTTTTTCAATTT.
```

The P43 promoter primers were:

```
GlmS-3F
                                          (SEQ ID No. 12)
GAAACACTGGCGGGCTGCCTTTTTCCGGGCGCTTAGTTTGATAGGTGG

TATGTTTTCGC;
```

```
GlmS-3R
                                          (SEQ ID No. 13)
CGTCCCCTCCTACATGTTTTTATAATGGTACCGCTATCAC.
```

The down-stream homologous fragment primers were:

```
GlmS-4F
                                          (SEQ ID No. 14)
GTGATAGCGGTACCATTATAAAAACATGTAGGAGGGGACG;

GlmS-R
                                           (SEQ ID No. 8)
TTCTGTCTCAAGTCCTCCATTGACG.
```

An up-stream homologous fragment, a P43 promoter and a down-stream homologous fragment were amplified from the genome of Bacillus subtilis by using the above primers, and a screening marker expression cassette containing spectinomycin resistance gene was amplified from the vector PDGREF. The T7 terminator sequence (TAGCATAAC-CCCTTGGGGCCTCTAAACGGGTCTT-GAGGGGTTTTTT, SEQ ID No. 28) was inserted into the primer GlmS-2F (SEQ ID No. 10). The up-stream homologous fragment, the screening marker, the P43 promoter and the down-stream homologous fragment were fused by fusion PCR technology, and a deleting cassette of glmS ribozyme encoding gene was obtained. The deleting cassette was amplified using the primer GlmS-F/GlmS-R, the obtained deleting cassette was transformed into Bacillus subtilis BSGN. The correct transformants were screened and determined by PCR validation. mazF was induced to express, and the strains without resistance were screened, the strains with glmS ribozyme deletion were obtained.

In this embodiment 2, the amplification conditions are as follows: pre-denaturation at 98° C. for 3 minutes; 34 cycles of (denaturation at 98° C. for 10 seconds, annealing at 55° C. for 5 seconds, and elongation at 68° C. for 1.2 min), and elongation at 68° C. for 5 minutes.

Embodiment 3

The amplification primers of the deleting cassette are designed based on the up-stream and down-stream sequences of glms ribozyme encoding gene of Bacillus subtilis (Bacillus subtilis 168, available from American Type Culture Collection, ATCC No. 27370) published in NCBI.

The up-stream homologous fragment primers were:

```
GlmS-F
                                           (SEQ ID No. 1)
TCTGCTATTATGCTGATGAACAC;

GlmS-1R
                                          (SEQ ID No. 15)
GGAATACTCAAAAAAAACACCCGCTTGTATAACGAGCGGATGGCC

TTTTTCCGGGCGCTTAGTT.
```

The screening marker expression cassette primers were:

```
GlmS-2F
                                          (SEQ ID No. 16)
GGAAAAAGGCCATCCGCTCGTTATACAAGCGGGTGTTTTTTTTGAGT

ATTCCAAACTGGACACATGG;
```

```
GlmS-2R
                                          (SEQ ID No. 17)
TGACTATGTGTACCGCGCAAAAACCAGTGTTTCCACCATTTTTTCAATTT.
```

The PsrfA promoter fragment primers were:

```
Psrf-F
                                          (SEQ ID No. 18)
AAATTGAAAAAATGGTGGAAACACTGGTTTTTGCGCGGTACACATAGTCA;

Psrf-R
                                          (SEQ ID No. 19)
CGTCCCCTCCTACATGTTTTCCCCTAATCTTTATAAGCAGTGAAC.
```

The down-stream homologous fragment primers were:

```
GlmS-4F
                                          (SEQ ID No. 20)
GTTCACTGCTTATAAAGATTAGGGGAAAACATGTAGGAGGGGACG;

GlmS-R
                                           (SEQ ID No. 8)
TTCTGTCTCAAGTCCTCCATTGACG.
```

An up-stream homologous fragment, a PsrfA promoter and a down-stream homologous fragment were amplified from the genome of Bacillus subtilis by using the above primers, and a screening marker expression cassette containing a spectinomycin resistance gene is amplified from the vector PDGREF. The ybc terminator sequence (CATC-CGCTCGTTATACAAGCGGGTGTTTTTTTT, SEQ ID No. 29) was inserted into the primer GlmS-2F (SEQ ID No. 16). The up-stream homologous fragment, the screening marker, the PsrfA promoter and the down-stream homologous fragment were fused by fusion PCR technology, and a deleting cassette of glmS ribozyme encoding gene was obtained. The deleting cassette was amplified using the primer GlmS-F/GlmS-R, the obtained deleting cassette was transformed into Bacillus subtilis BSGN. The correct transformants were screened and determined by PCR validation. mazF was induced to express, and the strains without resistance were screened, and the strains with glmS ribozyme deletion were obtained.

In this embodiment 3, the amplification conditions are as follows: pre-denaturation at 98° C. for 3 minutes; 34 cycles of (denaturation at 98° C. for 10 seconds, annealing at 55° C. for 5 seconds, and elongation at 68° C. for 1.2 min), and elongation at 68° C. for 5 minutes.

Embodiment 4

The amplification primers of the deleting cassette are designed based on the up-stream and down-stream sequences of glms ribozyme encoding gene of Bacillus subtilis (Bacillus subtilis 168, available from American Type Culture Collection, ATCC No. 27370) published in NCBI.

The up-stream homologous fragment primers were:

```
GlmS-F
                                           (SEQ ID No. 1)
TCTGCTATTATGCTGATGAACAC;

GlmS-1R
                                          (SEQ ID No. 21)
GGAATACTCAAAAAAGCCCGCTCATTAGGCGGGCTGCCTTTTTCCGGG

CGCTTAGTT.
```

The screening marker expression cassette primers were:

GlmS-2F
(SEQ ID No. 22)
GGAAAAAGGCAGCCCGCCTAATGAGCGGGCTTTTTTGAGATTCTACC
GTTCGTATAGC;

GlmS-2R
(SEQ ID No. 23)
GCGAAAACATACCACCTATCACTACCGTTCGTATAATGTATGC.

The P43 promoter primers were:

GlmS-3F
(SEQ ID No. 24)
GCATACATTATACGAACGGTAGTGATAGGTGGTATGTTTTCGC;

GlmS-3R
(SEQ ID No. 25)
CGTCCCCTCCTACATGTTTTTATAATGGTACCGCTATCAC.

The down-stream homologous fragment primers were:

GlmS-4F
(SEQ ID No. 26)
GTGATAGCGGTACCATTATAAAAACATGTAGGAGGGGACG;

GlmS-R
(SEQ ID No. 8)
TTCTGTCTCAAGTCCTCCATTGACG.

An up-stream homologous fragment, a P43 promoter and a down-stream homologous fragment were amplified from the genome of Bacillus subtilis by using the above primers, and a screening marker expression cassette containing bleomycin resistance gene was amplified from the vector P7Z6. The trp terminator sequence (AGCCCGCCTAAT-GAGCGGGCTTTTTT, SEQ ID No. 27) was inserted into the primer GlmS-2F (SEQ ID No. 22). The up-stream homologous fragment, the screening marker, P43 promoter and the down-stream homologous fragment were fused by fusion PCR technology, and a deleting cassette of glmS ribozyme encoding gene was obtained. The deleting cassette was amplified using the primer GlmS-F/GlmS-R, the obtained deleting cassette was transformed into Bacillus subtilis BSGN. The correct transformants were screened by PCR validation. mazF was induced to express, and the strains without resistance were screened, and the strains with glmS ribozyme deletion were obtained.

In this embodiment 4, the amplification conditions are as follows: pre-denaturation at 98° C. for 3 minutes; 34 cycles of (denaturation at 98° C. for 10 seconds, annealing at 55° C. for 5 seconds, and elongation at 68° C. for 1.2 min), and elongation at 68° C. for 5 minutes.

Embodiment 5

The Bacillus subtilis BSGNR constructed in embodiment 1 was cultured at 200 rpm under 37° C. The used seed medium comprises (by weight) tryptone 10 g/L, yeast powder 5 g/L and NaCl 10 g/L. The seeds were transferred into the fermentation medium at an inoculum size of 5%, and cultured at 200 rpm under 37° C. The fermentation medium comprises (by weight) glucose 2.0 g/L, $Na_2HPO_4$ 7.1 g/L, $KH_2PO_4$ 1.35 g/L, $(NH_4)_2SO_4$ 2 g/L, $MgSO_4$ 0.25 g/L, $FeSO_4.7H_2O$ 1.0 g/L, $MnSO_4.4H_2O$ 0.1 g/L, thymine 0.01 g/L and tryptophan 0.01 g/L. The content of acetylglucosamine in the fermentation supernatant was determined by HPLC.

HPLC detection method: Agilent 1200, RID detector, $NH_2$ column (250×4.6 mm, 5 μm), mobile phase: 70% acetonitrile, flow rate 0.75 mL/min, column temperature 30° C., injection volume: 10 μL.

FIG. 1 shows the effects of deletion of glmS ribozyme on cell growth and production of N-acetylglucosamine (GlcNAc). In FIG. 1a, cell growth result of strain BSGN is compared with glms ribozyme deletion strain BSGNR in a minimal medium wherein glucose is used as the sole carbon source. In FIG. 1b, GlcNAc titer of BSGN is compared with glms ribozyme deletion strain BSGNR in a shaking flask fermentation system, wherein in the used minimum medium glucose is used as the sole carbon source. In FIG. 1c, specific cell growth rate and GlcNAc productivity of BSGN is compared with glms ribozyme deletion strain BSGNR in a shaking flask fermentation system, wherein in the used minimum medium glucose is used as the sole carbon source. It can be seen from FIG. 1 that, The specific growth rate of the recombinant Bacillus subtilis BSGNR reaches 0.84 $h^{-1}$, acetylglucosamine in the fermentation supernatant reaches 321.3 mg/L, they are 2.09-fold and 2.57-fold of the original strains respectively, this shows that, by means of deletion of glms ribozyme encoding gene, the output of acetylglucosamine is greatly improved in recombinant Bacillus subtilis of the invention.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A recombinant *Bacillus subtilis* for producing acetylglucosamine, wherein the recombinant *Bacillus subtilis* is obtained by deletion of glmS ribozyme of *Bacillus subtilis* for regulating expression of glucosamine synthase, and insertion of a terminator and a constitutive promoter,
    wherein the terminator is a trp terminator having a nucleic acid sequence as shown in SEQ ID NO:27, a ybc terminator having a nucleic acid sequence as shown in SEQ ID NO:29, or a T7 terminator having a nucleic acid sequence as shown in SEQ ID NO:28,
    wherein the constitutive promoter is a P43 promoter, a PsrfA promoter or a PaprE promoter,
    wherein the P43 promoter is amplified by using a P43 promoter primer having a nucleic acid sequence as shown in SEQ ID NO:5, SEQ ID NO:6, SEQ ID NO:12, SEQ ID NO:13, SEQ ID NO:24, or SEQ ID NO:25, and
    wherein the PsrfA promoter is amplified by using a PsrfA promoter primer having a nucleic acid sequence as shown in SEQ ID NO:18 or SEQ ID NO:19.

2. The recombinant *Bacillus subtilis* as claimed in claim 1, wherein the *Bacillus subtilis* is obtained by controlling recombinant expression of glmS, GNA1 by promoters of $P_{xylA}$, $P_{43}$ respectively, taking *Bacillus subtilis* 168ΔnagPΔgamPΔgamAΔnagAΔnagBΔldhΔpta::lox72 as a host.

3. A construction method of a recombinant *Bacillus subtilis* for producing acetylglucosamine, comprising:
    (1) constructing a deleting cassette of a glmS ribozyme encoding gene, wherein the deleting cassette includes an upstream homologous fragment, a resistance gene, a terminator sequence, a constitutive promoter sequence and a downstream homologous fragment in sequence; and
    (2) transforming the deleting cassette of the step (1) into *Bacillus subtilis*, to obtain the recombinant *Bacillus subtilis*,
    wherein the upstream homologous fragment is amplified by using an up-stream homologous fragment primer having a nucleic acid sequence as shown in SEQ ID NO:1, SEQ ID NO:2, SEQ ID NO:9, SEQ ID NO:15, or SEQ ID NO:21,
    wherein the terminator is a trp terminator having a nucleic acid sequence as shown in SEQ ID NO:27, a ybc terminator having a nucleic acid sequence as shown in SEQ ID NO:29, or T7 terminator having a nucleic acid sequence as shown in SEQ ID NO:28,
    wherein the constitutive promoter is a P43 promoter or a PsrfA promoter,
    wherein the P43 promoter is amplified by using a P43 promoter primer having a nucleic acid sequence as shown in SEQ ID NO:5, SEQ ID NO:6, SEQ ID NO:12, SEQ ID NO:13, SEQ ID NO:24, or SEQ ID NO:25, and
    wherein the PsrfA promoter is amplified by using a PsrfA promoter primer having a nucleic acid sequence as shown in SEQ ID NO:18 or SEQ ID NO:19.

4. The construction method as claimed in claim 3, wherein in the step (1) the resistance gene is a spectinomycin resistance gene spc, a bleomycin resistance gene zeo, a kanamycin resistance gene kan, or an ampicillin resistance gene amp.

5. The construction method as claimed in claim 3, wherein the *Bacillus subtilis* is obtained by controlling recombinant expression of glmS, GNA1 by promoters of $P_{xylA}$, $P_{43}$ respectively, taking *Bacillus subtilis* 168ΔnagPΔgamPΔgamAΔnagAΔnagBΔldhΔpta::lox72 as a host.

6. The construction method as claimed in claim 3, wherein the downstream homologous fragment is amplified by using a downstream homologous fragment primer having a nucleic acid sequence as shown in SEQ ID NO:7, SEQ ID NO:8, SEQ ID NO:14, SEQ ID NO:20, or SEQ ID NO:26.

7. The construction method as claimed in claim 4, wherein the resistance gene is amplified by using a screen marker expression cassette primer having a nucleic acid sequence as shown in SEQ ID NO:3, SEQ ID NO:4, SEQ ID NO:10, SEQ ID NO:11, SEQ ID NO:16, SEQ ID NO:17, SEQ ID NO:22, or SEQ ID NO:23.

* * * * *

SEQUENCE LISTING

<160> NUMBER OF SEQ ID NOS: 29

<210> SEQ ID NO 1
<211> LENGTH: 23
<212> TYPE: DNA
<213> ORGANISM: Artificial sequence
<220> FEATURE:
<223> OTHER INFORMATION: Up-stream homologous fragment primer GlmS-F

<400> SEQUENCE: 1
tctgctatta tgctgatgaa cac                                          23

<210> SEQ ID NO 2

```
<211> LENGTH: 57
<212> TYPE: DNA
<213> ORGANISM: Aritical sequence
<220> FEATURE:
<223> OTHER INFORMATION: Up-stream homologous fragment primer GlmS-1R

<400> SEQUENCE: 2
ggaatactca aaaagcccg ctcattaggc gggctgcctt tttccgggcg cttagtt        57

<210> SEQ ID NO 3
<211> LENGTH: 60
<212> TYPE: DNA
<213> ORGANISM: Artificial sequence
<220> FEATURE:
<223> OTHER INFORMATION: Screening marker expression cassette primer
      GlmS-2F

<400> SEQUENCE: 3
ggaaaaaggc agcccgccta atgagcgggc tttttttgagt attccaaact ggacacatgg   60

<210> SEQ ID NO 4
<211> LENGTH: 59
<212> TYPE: DNA
<213> ORGANISM: Artificial sequence
<220> FEATURE:
<223> OTHER INFORMATION: Screening marker expression cassette primer
      GlmS-2R

<400> SEQUENCE: 4
atcaaactaa gcgcccggaa aaaggcagcc cgccagtgtt tccaccattt tttcaattt     59

<210> SEQ ID NO 5
<211> LENGTH: 59
<212> TYPE: DNA
<213> ORGANISM: Artificial sequence
<220> FEATURE:
<223> OTHER INFORMATION: P43 promoter primer GlmS-3F

<400> SEQUENCE: 5
gaaacactgg cgggctgcct ttttccgggc gcttagtttg ataggtggta tgttttcgc    59

<210> SEQ ID NO 6
<211> LENGTH: 40
<212> TYPE: DNA
<213> ORGANISM: Artificial sequence
<220> FEATURE:
<223> OTHER INFORMATION: P43 promoter primer GlmS-3R

<400> SEQUENCE: 6 cgtccctcc tacatgtttt tataatggta ccgctatcac                           40

<210> SEQ ID NO 7
<211> LENGTH: 40
<212> TYPE: DNA
<213> ORGANISM: Artificial sequence
<220> FEATURE:
<223> OTHER INFORMATION: Down-stream homologous fragment primer GlmS-4F

<400> SEQUENCE: 7
gtgatagcgg taccattata aaaacatgta ggaggggacg                          40

<210> SEQ ID NO 8
<211> LENGTH: 25
<212> TYPE: DNA
<213> ORGANISM: Artificial sequence
<220> FEATURE:
<223> OTHER INFORMATION: Down-stream homologous fragment primer GlmS-R
```

<210> SEQ ID NO 9
<211> LENGTH: 77
<212> TYPE: DNA
<213> ORGANISM: Artificial sequence
<220> FEATURE:
<223> OTHER INFORMATION: Up-stream homologous fragment primer GlmS-1R

<400> SEQUENCE: 9

```
ggaatactca aaaaccccct caagacccgt ttagaggccc caaggggtta tgctagcctt    60
tttccgggcg cttagtt                                                  77
```

<210> SEQ ID NO 10
<211> LENGTH: 80
<212> TYPE: DNA
<213> ORGANISM: Artificial sequence
<220> FEATURE:
<223> OTHER INFORMATION: Screening marker expression cassete primer
      GlmS-2F

<400> SEQUENCE: 10

```
ggaaaaaggc tagcataacc ccttgggggcc tctaaacggg tcttgagggg ttttttgagt    60
attccaaact ggacacatgg                                               80
```

<210> SEQ ID NO 11
<211> LENGTH: 59
<212> TYPE: DNA
<213> ORGANISM: Artificial sequence
<220> FEATURE:
<223> OTHER INFORMATION: Screening marker expression cassete primer
      GlmS-2R

<400> SEQUENCE: 11

```
atcaaactaa gcgcccggaa aaaggcagcc cgccagtgtt tccaccattt tttcaattt     59
```

<210> SEQ ID NO 12
<211> LENGTH: 59
<212> TYPE: DNA
<213> ORGANISM: Artificial sequence
<220> FEATURE:
<223> OTHER INFORMATION: P43 promoter primer GlmS-3F

<400> SEQUENCE: 12

```
gaaacactgg cgggctgcct ttttccgggc gcttagtttg ataggtggta tgttttcgc     59
```

<210> SEQ ID NO 13
<211> LENGTH: 40
<212> TYPE: DNA
<213> ORGANISM: Artificial sequence
<220> FEATURE:
<223> OTHER INFORMATION: P43 promoter primer GlmS-3R

<400> SEQUENCE: 13

```
cgtccccctcc tacatgtttt tataatggta ccgctatcac                        40
```

<210> SEQ ID NO 14
<211> LENGTH: 40
<212> TYPE: DNA
<213> ORGANISM: Artificial sequence
<220> FEATURE:
<223> OTHER INFORMATION: Down-stream homologous fragment primer GlmS-4F

<400> SEQUENCE: 14
gtgatagcgg taccattata aaaacatgta ggaggggacg                          40

<210> SEQ ID NO 15
<211> LENGTH: 64
<212> TYPE: DNA
<213> ORGANISM: Artificial sequence
<220> FEATURE:
<223> OTHER INFORMATION: Up-stream homologous fragment primer GlmS-1R

<400> SEQUENCE: 15
ggaatactca aaaaaaacac ccgcttgtat aacgagcgga tggcctttt ccgggcgctt    60 agtt                                                                64

<210> SEQ ID NO 16
<211> LENGTH: 67
<212> TYPE: DNA
<213> ORGANISM: Artificial sequence
<220> FEATURE:
<223> OTHER INFORMATION: Screening marker expression cassette primer
      GlmS-2F

<400> SEQUENCE: 16
ggaaaaaggc catccgctcg ttatacaagc gggtgttttt tttgagtatt ccaaactgga    60
cacatgg                                                             67

<210> SEQ ID NO 17
<211> LENGTH: 50
<212> TYPE: DNA
<213> ORGANISM: Artificial sequence
<220> FEATURE:
<223> OTHER INFORMATION: Screening marker expression cassette primer
      GlmS-2R

<400> SEQUENCE: 17
tgactatgtg taccgcgcaa aaccagtgt ttccaccatt ttttcaattt               50

<210> SEQ ID NO 18
<211> LENGTH: 50
<212> TYPE: DNA
<213> ORGANISM: Artificial sequence
<220> FEATURE:
<223> OTHER INFORMATION: PsrfA promoter fragment primer Psrf-F

<400> SEQUENCE: 18
aaattgaaaa aatggtggaa acactggttt ttgcgcggta cacatagtca               50

<210> SEQ ID NO 19
<211> LENGTH: 45
<212> TYPE: DNA
<213> ORGANISM: Artificial sequence
<220> FEATURE:
<223> OTHER INFORMATION: PsrfA promoter fragment primer Psrf-R

<400> SEQUENCE: 19
cgtcccctcc tacatgtttt cccctaatct ttataagcag tgaac                    45

<210> SEQ ID NO 20
<211> LENGTH: 45
<212> TYPE: DNA
<213> ORGANISM: Artificial sequence
<220> FEATURE:
<223> OTHER INFORMATION: Down-stream homologous fragment primer GlmS-4F

<400> SEQUENCE: 20
gttcactgct tataaagatt aggggaaaac atgtaggagg ggacg    45

<210> SEQ ID NO 21
<211> LENGTH: 57
<212> TYPE: DNA
<213> ORGANISM: Artificial sequence
<220> FEATURE:
<223> OTHER INFORMATION: Up-stream homologous fragment primer GlmS-1R

<400> SEQUENCE: 21
ggaatactca aaaagcccg ctcattaggc gggctgcctt tttccgggcg cttagtt    57

<210> SEQ ID NO 22
<211> LENGTH: 58
<212> TYPE: DNA
<213> ORGANISM: Artificial sequence
<220> FEATURE:
<223> OTHER INFORMATION: Screening marker expression cassette primer
      GlmS-2F

<400> SEQUENCE: 22
ggaaaaaggc agcccgccta atgagcgggc ttttttgaga ttctaccgtt cgtatagc    58

<210> SEQ ID NO 23
<211> LENGTH: 43
<212> TYPE: DNA
<213> ORGANISM: Artificial sequence
<220> FEATURE:
<223> OTHER INFORMATION: Screening marker expression cassette primer
      GlmS-2R

<400> SEQUENCE: 23
gcgaaaacat accacctatc actaccgttc gtataatgta tgc    43

<210> SEQ ID NO 24
<211> LENGTH: 43
<212> TYPE: DNA
<213> ORGANISM: Artificial sequence
<220> FEATURE:
<223> OTHER INFORMATION: P43 promoter primer GlmS-3F

<400> SEQUENCE: 24
gcatacatta tacgaacggt agtgataggt ggtatgtttt cgc    43

<210> SEQ ID NO 25
<211> LENGTH: 40
<212> TYPE: DNA
<213> ORGANISM: Artificial sequence
<220> FEATURE:
<223> OTHER INFORMATION: P43 promoter primer GlmS-3R

<400> SEQUENCE: 25
cgtcccctcc tacatgtttt tataatggta ccgctatcac    40

<210> SEQ ID NO 26
<211> LENGTH: 40
<212> TYPE: DNA
<213> ORGANISM: Artificial sequence
<220> FEATURE:
<223> OTHER INFORMATION: Down-stream homologous fragment primer GlmS-4F

<400> SEQUENCE: 26
gtgatagcgg taccattata aaaacatgta ggaggggacg    40

<210> SEQ ID NO 27

```
<211> LENGTH: 26
<212> TYPE: DNA
<213> ORGANISM: Artificial sequence
<220> FEATURE:
<223> OTHER INFORMATION: trp terminator

<400> SEQUENCE: 27
agcccgccta atgagcgggc tttttt                                           26

<210> SEQ ID NO 28
<211> LENGTH: 46
<212> TYPE: DNA
<213> ORGANISM: Artificial sequence
<220> FEATURE:
<223> OTHER INFORMATION: T7 terminator

<400> SEQUENCE: 28
tagcataacc ccttggggcc tctaaacggg tcttgagggg tttttt                     46

<210> SEQ ID NO 29
<211> LENGTH: 33
<212> TYPE: DNA
<213> ORGANISM: Artificial sequence
<220> FEATURE:
<223> OTHER INFORMATION: ybc terminator

<400> SEQUENCE: 29
catccgctcg ttatacaagc gggtgttttt ttt                                   33
```